United States Patent
DeToro et al.

(10) Patent No.: US 8,062,243 B2
(45) Date of Patent: Nov. 22, 2011

(54) ORTHOTIC DEVICE FOR A PIVOTING JOINT OF THE HUMAN BODY

(75) Inventors: William W. DeToro, Poland, OH (US); Brian S. Perala, Warren, OH (US); William A. DeToro, Poland, OH (US); Jack N. Huey, Poland, OH (US)

(73) Assignee: Anatomical Concepts, Inc., Poland, OH (US)

( * ) Notice: Subject to any disclaimer, the term of this patent is extended or adjusted under 35 U.S.C. 154(b) by 750 days.

(21) Appl. No.: 12/215,733

(22) Filed: Jun. 30, 2008

(65) Prior Publication Data

US 2009/0326426 A1    Dec. 31, 2009

(51) Int. Cl.
*A61F 5/00* (2006.01)

(52) U.S. Cl. .................. 602/16; 602/23; 602/27; 602/28

(58) Field of Classification Search ................ 602/5, 12, 602/16, 19–23, 27–29; 482/79–80; 16/374–375; 36/117.1, 117.4, 118.2, 118.7–118.9, 140, 36/155–156, 158, 160
See application file for complete search history.

(56) References Cited

U.S. PATENT DOCUMENTS

| | | | |
|---|---|---|---|
| 1,332,047 A | 2/1920 | Lasher | |
| 1,598,504 A | 8/1926 | Pierce et al. | |
| 2,439,100 A | 4/1948 | Richards | |
| 2,444,839 A | 7/1948 | Markkula | |
| 2,525,237 A | 10/1950 | Park | |
| 2,663,294 A | 12/1953 | Harrison | |
| 2,847,991 A | 8/1958 | Andrews | |
| 2,874,690 A | 2/1959 | Cowgill | |
| 3,527,209 A | 9/1970 | Baker | |
| 3,543,421 A * | 12/1970 | Ader | 36/118.8 |
| 3,986,501 A | 10/1976 | Schad | |
| 4,329,982 A | 5/1982 | Heaney | |
| 4,566,447 A | 1/1986 | Deis | |
| 4,651,723 A | 3/1987 | Satoh | |
| 4,817,589 A | 4/1989 | Wertz | |
| 5,031,341 A * | 7/1991 | Paris et al. | 36/118.8 |
| 5,070,868 A * | 12/1991 | Hepburn et al. | 602/27 |
| 5,088,479 A | 2/1992 | DeToro | |
| 5,224,925 A | 7/1993 | Varn | |
| 5,259,834 A | 11/1993 | Wittmeyer | |
| 5,302,169 A | 4/1994 | Taylor | |
| 5,382,224 A | 1/1995 | Spangler | |
| 5,486,157 A * | 1/1996 | DiBenedetto | 602/27 |
| 5,545,127 A | 8/1996 | DeToro | |
| 5,593,383 A | 1/1997 | DeToro | |
| 5,848,983 A * | 12/1998 | Basaj et al. | 602/22 |
| 5,908,398 A | 6/1999 | DeToro | |
| 5,944,679 A | 8/1999 | DeToro | |
| 6,102,881 A | 8/2000 | Quackenbush et al. | |
| 6,302,858 B1 * | 10/2001 | DeToro et al. | 602/5 |

(Continued)

*Primary Examiner* — Patricia Bianco
*Assistant Examiner* — Kari Petrik
(74) *Attorney, Agent, or Firm* — Robert J. Herberger

(57) ABSTRACT

An orthotic device for a joint of the human body, at which a body part pivots, includes first, second and third members. A first connection joins the first member and the second member and defines a first axis about which the first member and the second member pivot through an adjustable range of angular motion. A second connection joins the second member and the third member, defines a second axis substantially parallel to the first axis about which the second member and the third member pivot through a second range of angular motion, and includes a limit to plantar flexion about the second axis.

17 Claims, 7 Drawing Sheets

U.S. PATENT DOCUMENTS

| | | |
|---|---|---|
| 6,350,246 B1 | 2/2002 | DeToro et al. |
| 6,377,178 B1 | 4/2002 | DeToro et al. |
| 6,464,659 B1 | 10/2002 | DeToro et al. |
| 6,793,638 B1 | 9/2004 | DeToro et al. |
| 7,011,641 B1 | 3/2006 | DeToro et al. |
| 7,112,181 B1 | 9/2006 | DeToro et al. |
| 7,122,016 B1 | 10/2006 | DeToro et al. |
| 7,682,322 B2 * | 3/2010 | Engelman ............... 602/16 |

* cited by examiner

ORTHOTIC DEVICE FOR A PIVOTING JOINT OF THE HUMAN BODY

BACKGROUND OF THE INVENTION

1. Field of the Invention

This invention relates generally to an orthotic device, and particularly to an orthotic that provides adjustable control of a range of angular motion at a joint of the human body where pivoting normally occurs.

2. Description of the Prior Art

An orthotic is a device, such as a brace or splint, for supporting, immobilizing, or treating muscles, joints, or skeletal parts, which are weak, ineffective, deformed, or injured. To assist in restoring a joint of the human body to normal, effective function, the joint may be restricted for a period by an orthotic, which imposes a fixed pivoted position. Or an orthotic may permit adjustable angular displacement of the joint, which is retained for a period by the orthotic and gradually increased at intervals to improve the pivotal range of use.

An orthotic that can be adjusted at multiple, mutually spaced locations to enhance the range of flexibility and use of the joint provides an added advantage.

A need exists for an orthotic device that enhances ambulation and heel suspension, and allows multiple ranges of pivotal movement about respective spaced axes during various stages of therapy. Preferably, a range of movement about a first axis is adjusted reliably and easily by releasing an attachment, changing the angular displacement of the orthotic about the first axis to a new, desired orientation, and securing the orthotic in the desired angular disposition by reengaging the attachment. The range of movement about a second axis may be limited reliably by mutual contact between stop surfaces located on opposite sides of a second axis.

SUMMARY OF THE INVENTION

An orthotic device for a joint of the human body, at which a body part pivots, includes first, second and third members. A first connection joins the first member and the second member and defines a first axis about which the first member and the second member pivot through an adjustable range of angular motion. A second connection joins the second member and the third member, defines a second axis substantially parallel to the first axis about which the second member and the third member pivot through a second range of angular motion, and includes a limit to the second range of angular motion to limit plantar flexion or angular movement about the second axis.

The orthotic is manufactured from lightweight materials, e.g., aluminum and plastic, which are formed by conventional techniques and at low cost. The aluminum may be roll formed or forged; the plastic may be molded.

The orthotic device provides multiple ranges of pivotal movement about respective spaced axes. The range of movement about a first axis is adjusted reliably and easily by releasing a threaded attachment, changing the angular displacement of the orthotic about the first axis to a new, desired orientation, and securing the orthotic in the desired angular disposition by reengaging the attachment. The range of movement about the second axis is limited by mutual contact between stop surfaces located on opposite sides of the second axis.

The scope of applicability of the preferred embodiment will become apparent from the following detailed description, claims and drawings. It should be understood, that the description and specific examples, although indicating preferred embodiments of the invention, are given by way of illustration only. Various changes and modifications to the described embodiments and examples will become apparent to those skilled in the art.

DESCRIPTION OF THE DRAWINGS

Having generally described the nature of the invention, reference will now be made to the accompanying drawings used to illustrate and describe the preferred embodiments thereof. Further, these and other advantages will become apparent to those skilled in the art from the following detailed description of the embodiments when considered in the light of these drawings in which.

DESCRIPTION OF THE PREFERRED EMBODIMENT

Figures 1, 2:
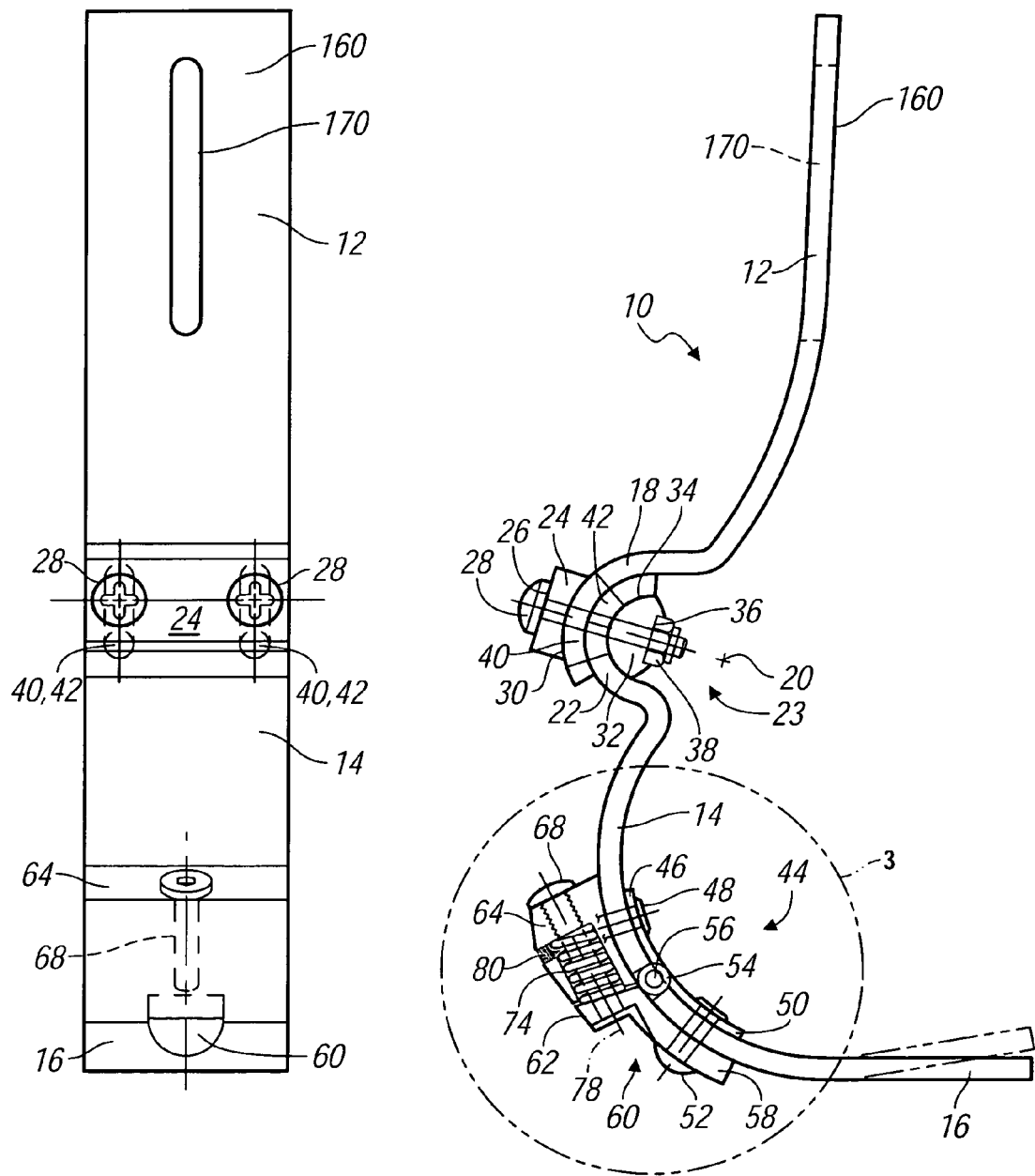
FIG. 1 is a rear view of a device of an orthotic.
FIG. 2 is a side view of FIG. 1.
Figure 3:
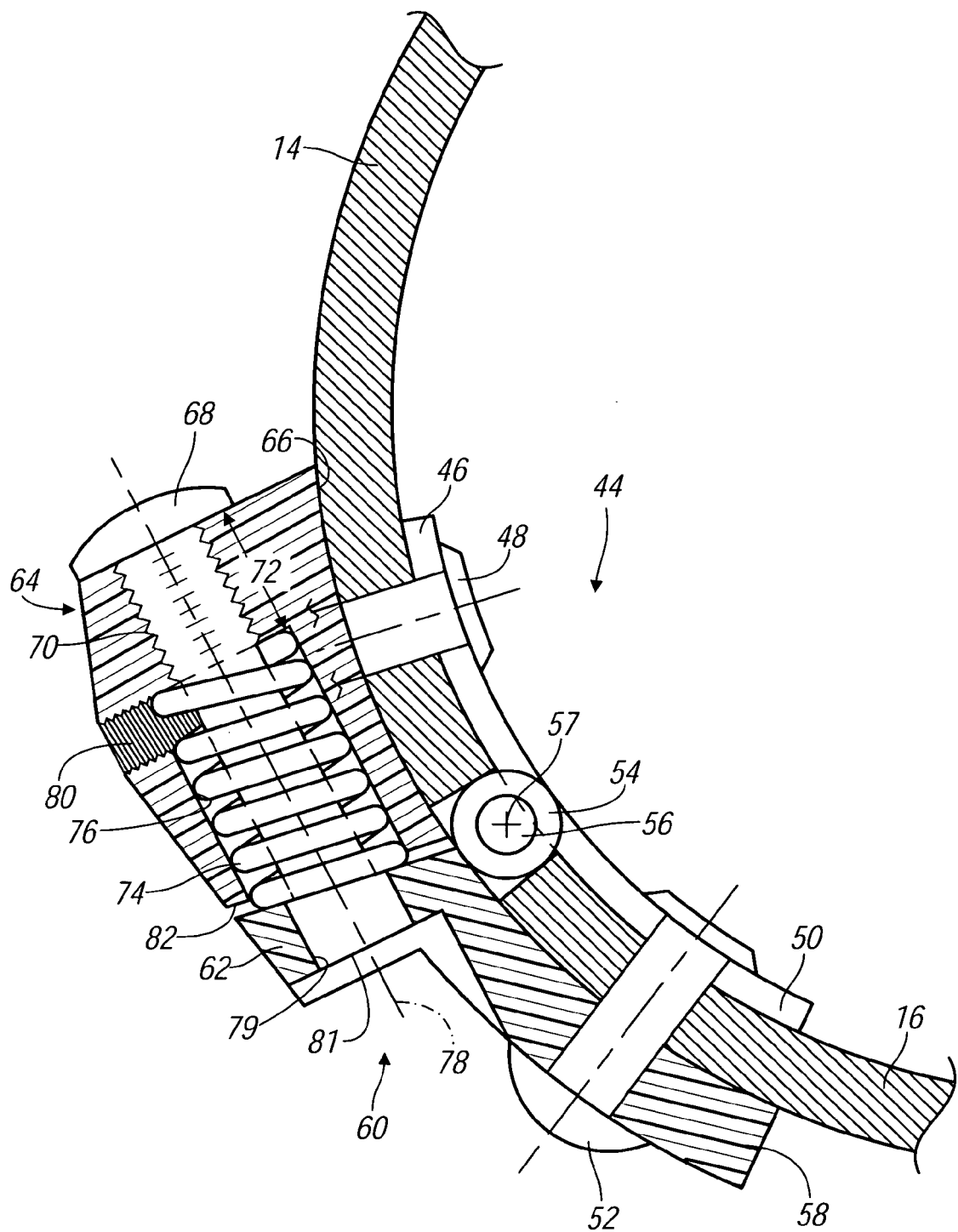
FIG. 3 is a cross sectional side view to a larger scale of the lower connection shown in FIG. 1.

Referring now to FIGS. 1 through 3, an orthotic device 10 includes an upper member 12, intermediate member 14 and lower member 16, each member preferably being of aluminum or another structural material having density, strength and endurance comparable to those of aluminum.

The lower end of the upper member 12 is formed with a circular arc 18 having a center 20. The upper end of intermediate member 14 is formed with a circular arc 22, which is centered at 20 and whose outer surface nests within the inner surface of arc 18. Members 12 and 14 are connected mutually at an adjustable connection 23. An outer block 24 is formed with a flat outer surface 26, engaged by the head of threaded attachment 28, e.g., a screw or bolt 28, and a circular cylindrical inner surface 30 centered at 20. An inner block 32 is formed with a circular cylindrical outer surface 34 centered at 20, and a flat inner surface 36 contacted by self-locking nuts 38, each nut engaging a respective attachment 28. The upper member 12 is formed with two parallel slotted holes 40. The intermediate member 14 is formed with two slotted holes 42, each hole 42 being aligned with a respective hole 40. Each attachment 28 extends through a hole in the outer block 24, a pair of holes 40, 42 in members 12 and 14, and a hole in the inner block 32.

The lower portion of intermediate member 14 and the upper portion of lower member 16 are formed with arcuate surfaces, which together form an arc that is continuous across a lower connection 44. A first hinge plate 46 is secured to member 14 by rivets 48, and a second hinge plate 50 is secured to member 16 by rivets 52. The lugs 54 of hinge plate 46 straddle the center lug of hinge plate 50. Those lugs and the hinge pin 56 that connects them are located between the ends of members 14 and 16. Therefore, lower member 16 must pivot counterclockwise about the axis 57 of the hinge pin 56 from the fully extended position shown in FIGS. 2 and 3, but it can pivot in either direction other than from the fully extended position.

In operation, the angular disposition of the first or upper connection 23 is adjusted by loosing the engagement of nuts 38 with screws 28 sufficiently to permit the arcuate surfaces 18, 22 of members 12, 14 to rotate about center 20 as the slotted holes 40, 42 slide relative the attachments. When the desired angular position is established, the nuts 38 and screws 28 are tightened, which draws blocks 24, 32 and the arcuate surfaces 18, 22 of members 12, 14 into friction contact and secures the desired angular setting of the upper connection 23.

One leg 58 of an angle bracket 60 is secured by rivets 52 to the lower member 16. Another leg 62 of bracket 60 is located near and facing a bracket 64, which is secured to the intermediate member 14 by rivets 48 having a head counterbored in bracket 64. The inner surface 66 of bracket 64 conforms to the contour of intermediate member 14. Preferably, angle bracket 60 and bracket 64 are formed of plastic material.

Bracket 64 supports an adjustment screw 68 having screw threads 70 that extend along the screw shank and are aligned with axis 78. The threads 70 of screw 68 engage internal screw threads, which are tapped along a length 72 of bracket 64. A compression helical spring 74 is located in a bore 76, aligned with axis 78 and formed in bracket 64. Spring 74 is secured in its position in the bore 76 by a set screw 80, which is threaded into bracket 64 and engages consecutive loops of the spring 74.

Bracket 60 pivots about axis 57 when screw 68 is inserted in bracket 64 with its head at the upper end of bracket 64 and its screw threads engaged with the internal screw threads in bracket 64, as shown in FIGS. 2 and 3. In this configuration, screw 68 is held in place by the engaged screw threads, and its shank acts as a guide to maintain the spring aligned with bore 76 when spring 74 extends past the end face 82 of bracket 64, and the spring elastically opposes and prevents contact between bracket 60 and bracket 64. The diameter of bore 79 in bracket 62 is larger than the diameter of the shank of screw 68, so that the screw has no contact with the bore 79 or bracket 60 when the device 10 is assembled to permit bracket 60 to pivot. Notably, bracket 60 can pivot freely (without resistance) about axis 57, except to the point of contact with spring 74, and ultimately comes to a stop when bracket 60 finally contacts the end face 82 of bracket 64.

Pivoting of bracket 60 about axis 57 is locked out or prevented when the device 10 is assembled such that the head of screw 68 is seated in a counterbore 81 in the leg 62 of bracket 60. Specifically, the screw shank extends through bore 79 in bracket 60 and bore 76 in bracket 64, and its screw threads engaged the internal screw threads in bracket 64 along length 72. When assembled in this way, bracket 60 contacts the end face 82 of bracket 64 and screw 68 holds bracket 60 closed and unable to pivot.

Figure 4:
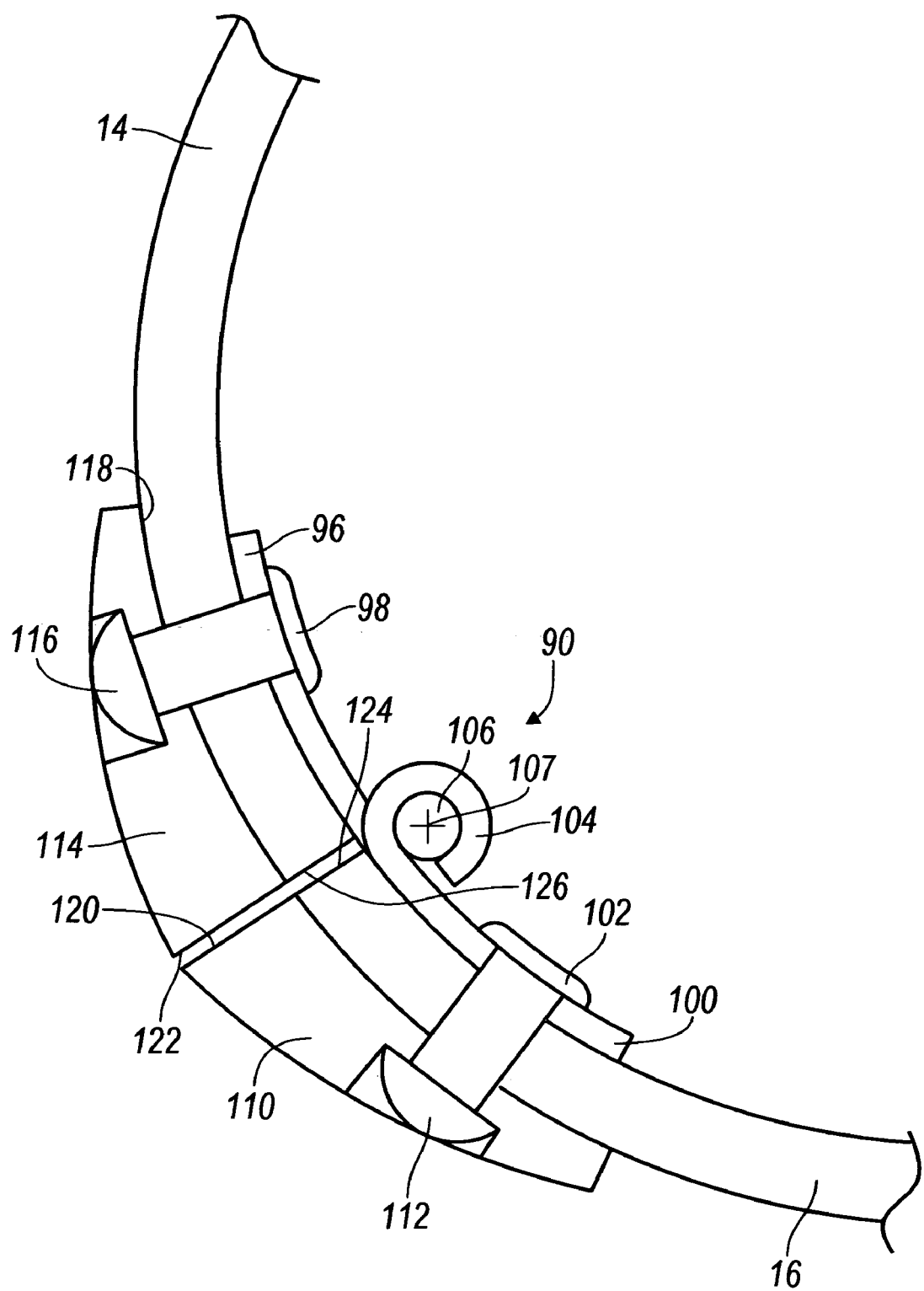
FIG. 4 is a side view of an alternate embodiment of the lower connection.

FIG. 4 illustrates an alternative lower connection 90 of an orthotic, which is included with the upper member 12, intermediate member 14, lower member 16, and upper connection 23, substantially as described with reference to FIGS. 1 through 3.

The lower portion of intermediate member 14 and the upper portion of lower member 16 are formed with arcuate surfaces, which together form an arc that is continuous across the lower connection 90. A first hinge plate 96 is secured to intermediate member 14 by rivets 98, and a second hinge plate 100 is secured to lower member 16 by rivets 102. Two lugs 104 of hinge plate 100 straddle the center lug of hinge plate 96. Those lugs and the hinge pin 106 that connects them are located eccentric of the ends of members 14 and 16 and concentric with an axis 107, about which the lower connection 90 pivots.

A bracket 110 is secured to the lower member 16 by rivets 102, each rivet having a head 112 that is counterbored from the outer surface in bracket 110. Bracket 110 is located near and facing a bracket 114, which is secured to the intermediate member 14 by rivets 98, each rivet having a head 116 that is counterbored from the outer surface in bracket 114. The inner surface 118 of bracket 114 conforms to the contour of intermediate member 14. Preferably, bracket 110 and bracket 114 are formed of plastic material.

When the lower member 16 pivots clockwise about axis 107 to the fully extended position, the adjacent end faces 120, 122 of brackets 110 and 114, respectively, become engaged by mutually contact, such that the contact provides a resistance stop to prevent further clockwise pivoting of the lower member 16 about axis 107, thereby limiting plantar flexion, i.e. movement that increases the angle between the foot and the leg, for treatment of drop foot especially in a stroke patient. The lower member 16 must pivot about the axis 107 of hinge pin 106 counterclockwise from the fully extended position, but it can pivot in either direction other than from the fully extended position.

In a third embodiment, brackets 110 and 114 can be deleted from the lower connection 90 illustrated in FIG. 4. The first hinge plate 96 is secured to lower member 14 by the rivets 98 and the second hinge plate 100 is directly secured to intermediate member 16 by the rivets 102. Two lugs 104 of hinge plate 100 straddle the center lug of hinge plate 96, and those lugs and the hinge pin 106 that connects them are located eccentric with the ends of members 14 and 16. Therefore, in this third embodiment, when the lower member 16 pivots clockwise to the fully extended position, the adjacent end faces 124, 126 of members 16 and 14, respectively, become engaged by mutually contact, which provides a resistance stop to prevent further clockwise pivoting of the lower member 16 about axis 107. The lower member 16 must pivot about the axis 107 of hinge pin 106 counterclockwise from the fully extended position shown in FIG. 4, but it can pivot in either direction other than from the fully extended position.

Figure 5:
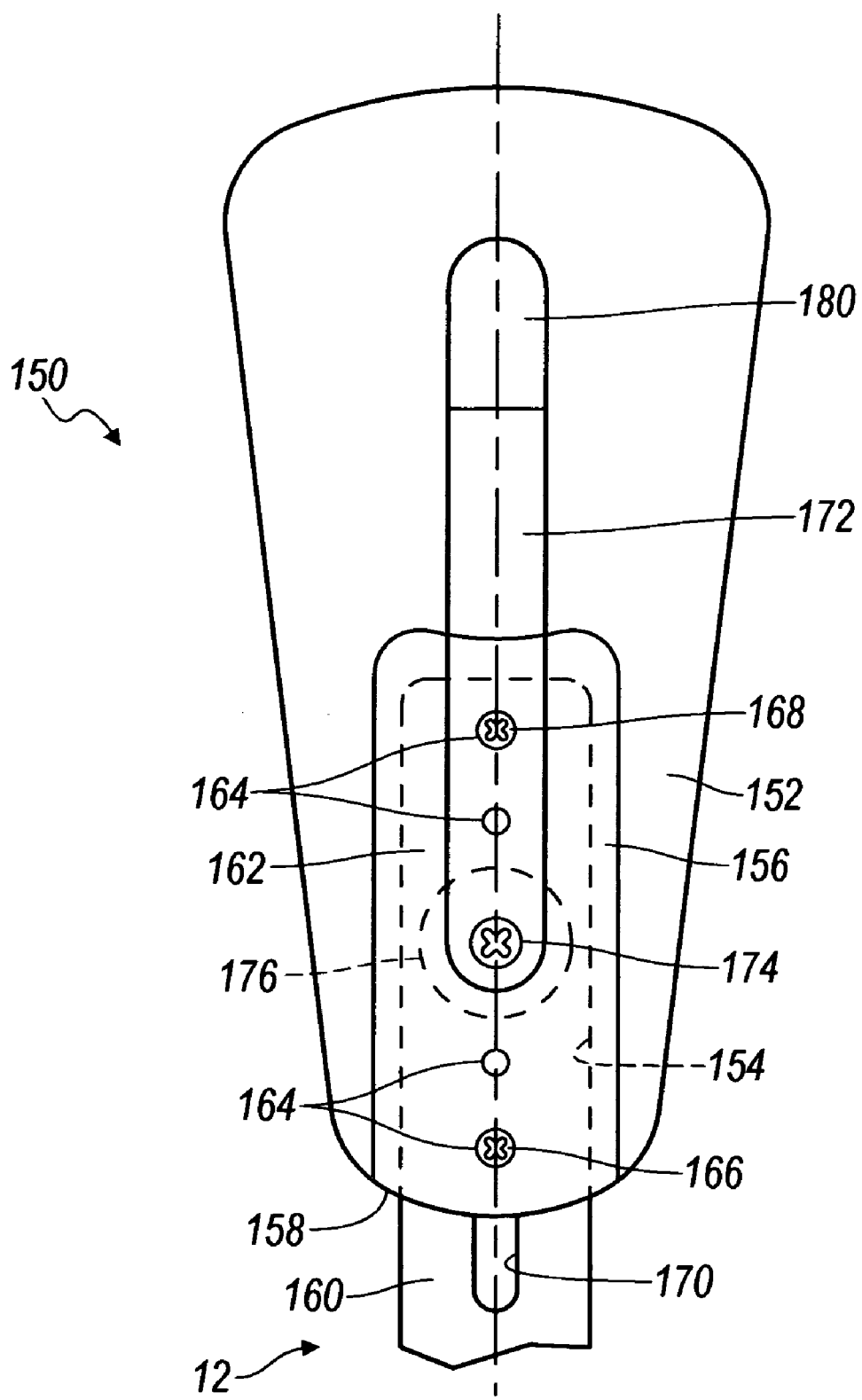
FIG. 5 is a rear view of a leg support, into which the orthotic device of FIG. 1 can be inserted and retained.
Figure 6:
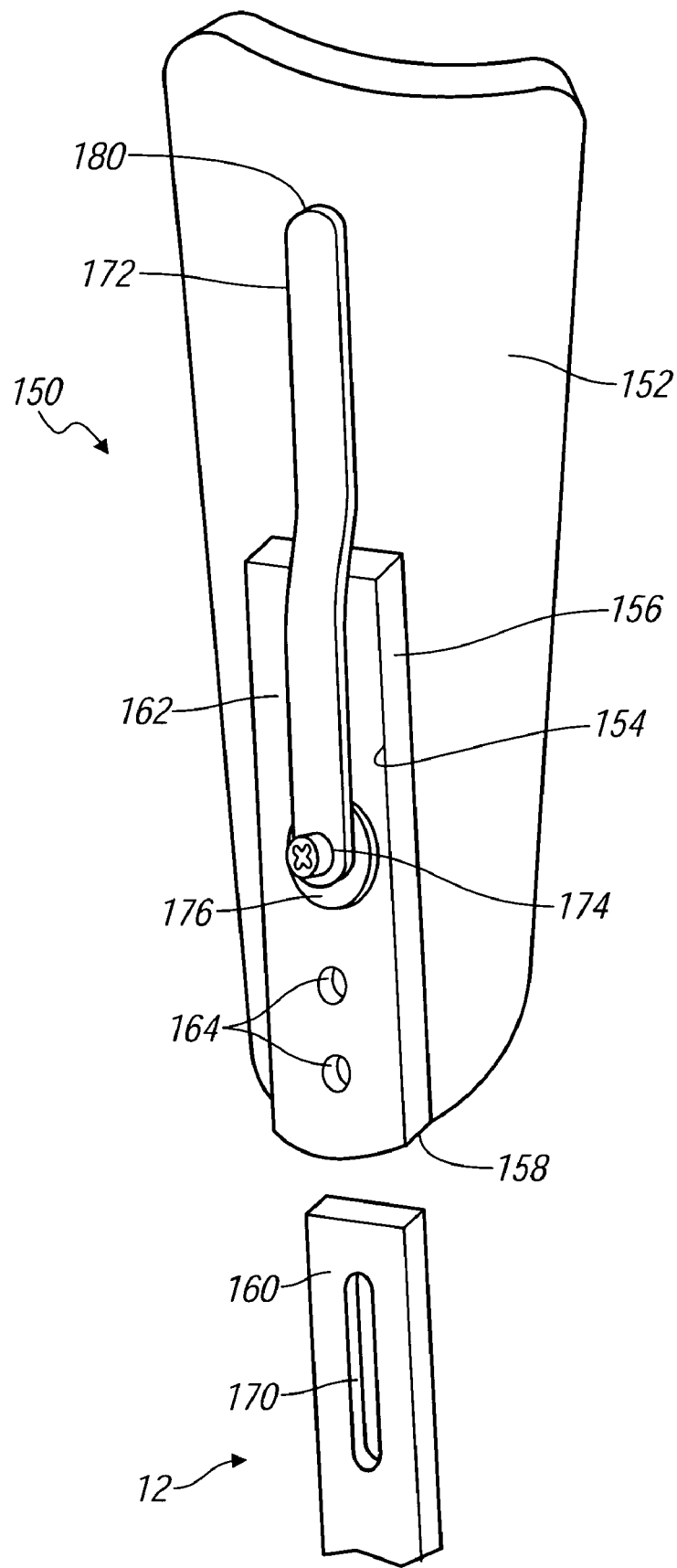
FIG. 6 is a perspective view of the leg support of FIG. 5.

FIGS. 5 and 6 show a brace or support 150, which includes a front or inner surface that conforms to the contour of the calf of the human leg, and an outer surface 152, which is substantially parallel to its inner surface. The outer surface 152 is formed with a hollow pocket 154 enclosed by a wall 156 and having an opening 158, into which the upper end 160 of the upper member 12 is inserted. The outer surface 162 of the pocket 154 has a series of holes 164, which extend through the pocket and the inner and outer surfaces of the support 150. Threaded attachments 166, 168, inserted through at least some of the holes 164 and through a slotted hole 170 in the upper member 12, secure the support 150 and upper member 12 in a desired position.

A rotating bar 172, in the form of a thin elongated plate, is secured at one end by an attachment 174 to a boss 176 formed on the outer surface 162 of pocket 154. The opposite end 180 of the rotating bar 172 bears against the outer surface 152 when the rotating bar is not in use. The rotating bar 172 can be rotated in either direction about attachment 174 from the position shown in FIG. 5, such that the area of the rotating bar near its end 180 contacts a surface, e.g., the surface of a bed in which the user is lying, to prop the foot against rotation from a desired position, usually in the vertical plane.

Figure 7:
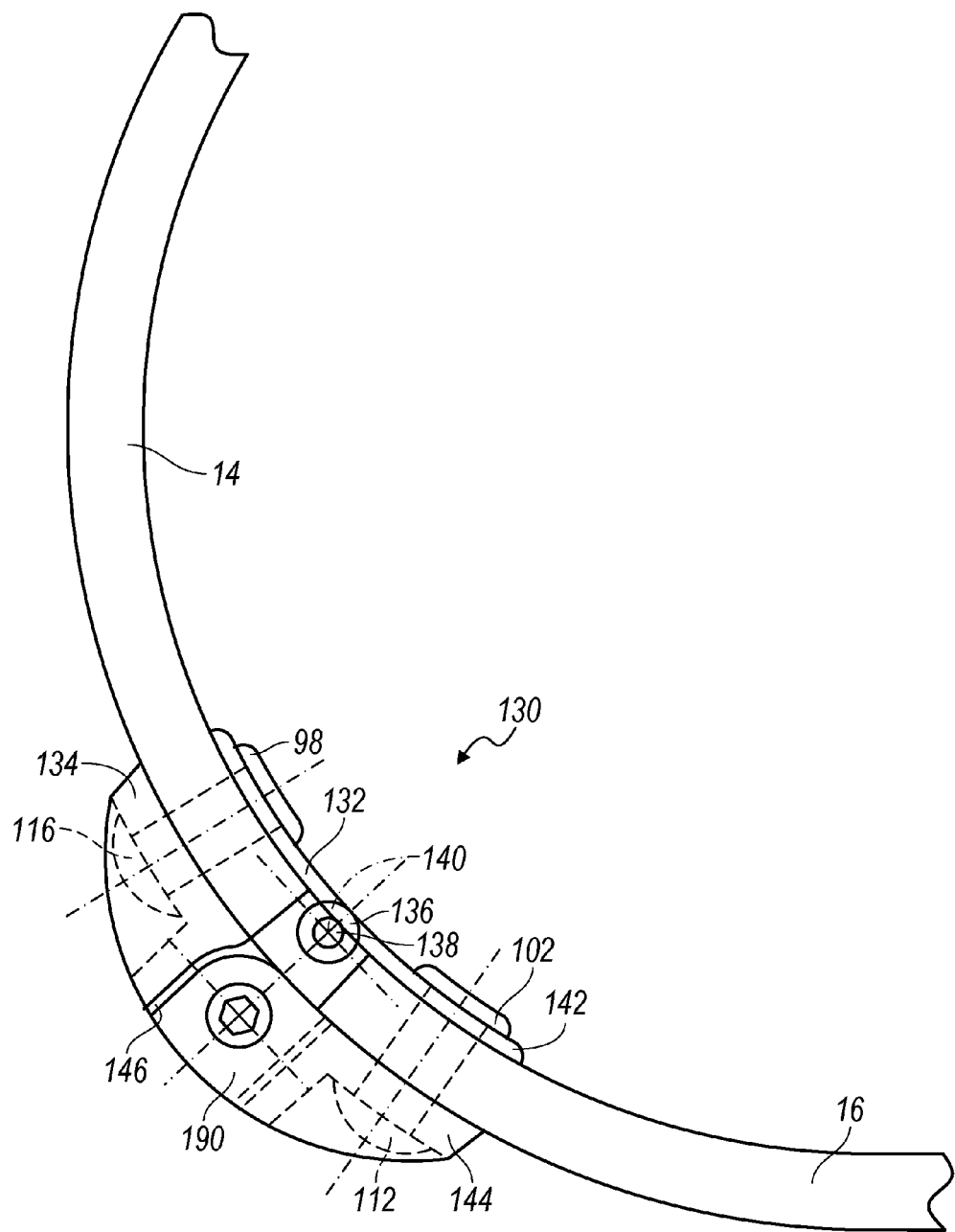
FIG. 7 is a side view of yet another embodiment of the lower connection.
Figure 8:
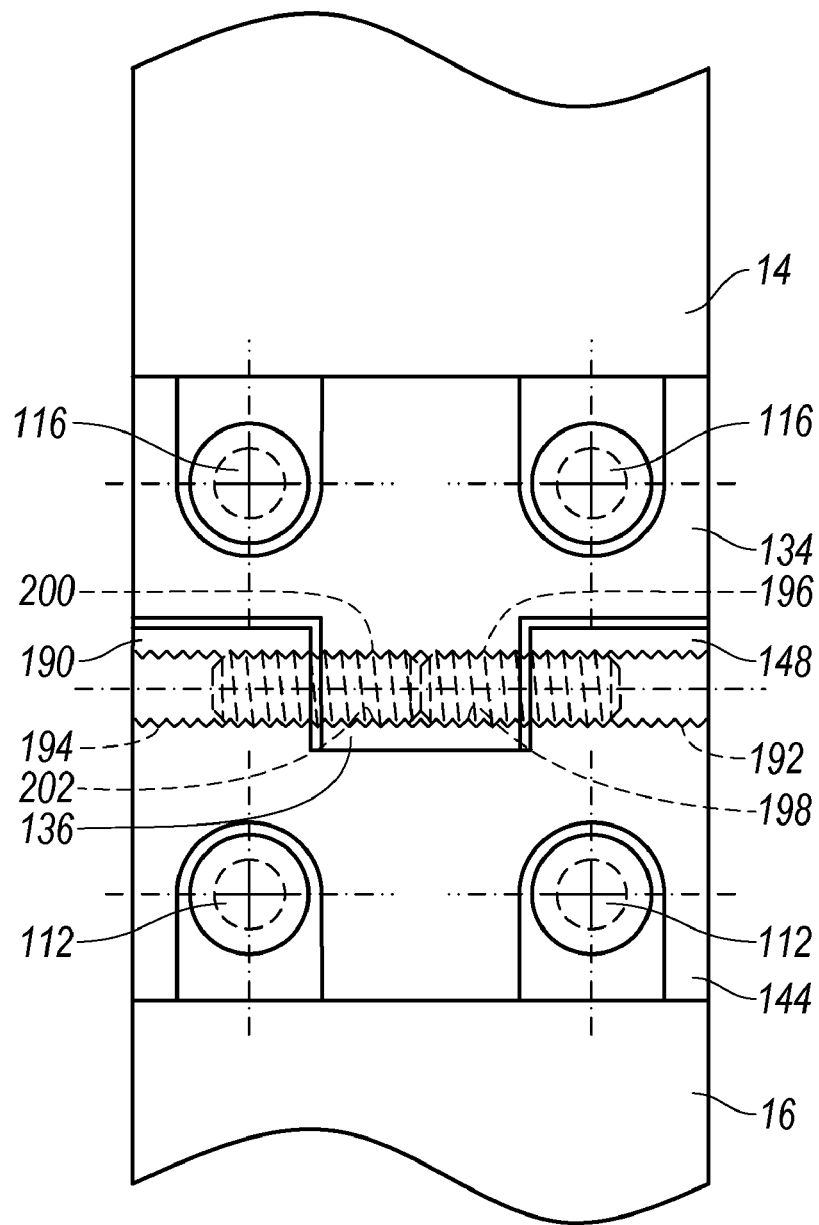
FIG. 8 is a rear view of the lower connection of FIG. 7.

In a fourth embodiment of the lower connection 130 illustrated in FIGS. 7 and 8, a first hinge plate 132, secured by rivets 98 to intermediate member 14 and bracket 134, terminates in a lug 136, which surrounds a hinge pin 138 centered at a pivot axis 140. A second hinge plate 142, secured by rivets 102 to lower member 16 and bracket 144, terminates at mutually spaced lugs, which straddle lug 136 and surround hinge pin 138.

As best seen in FIG. 8, bracket 134 terminates in a central lug 146, located between two lugs 148, 190, which are formed on bracket 144 and straddle lug 146. A lateral hole in lug 148 is formed with screw threads 192, which extend across the width of lug 148. A lateral hole in lug 190 is formed with screw threads 194, which are aligned with threads 192 and extend across the width of lug 190. When the lower member 16 pivots clockwise to the fully extended position, a set screw 196 engaged with screw threads 192 can be threaded from one lateral direction into lug 148 such that the set screw enters a hole 198 in lug 146, and a set screw 200 engaged with screw threads 194 can be threaded in the opposite lateral direction into lug 190 such that the set screw enters a hole 202 in lug 146, which is preferably aligned with the hole in lug 148. Engagement of the set screws 196, 200 with lugs 146, 148, 190 secures members 16, 14 mutually and provides a resistance stop that locks out any pivoting of the lower member 16 about axis 140. Otherwise, the lower member 16 pivots about the axis 140 counterclockwise from the fully extended position shown in FIGS. 7 and 8, and can pivot in either direction other than from the fully extended position.

Notably, by locking out the free motion of the ankle at axis 57 or 140, as the case may be, the brace will transfers a floor reaction moment to the knee, which will cause the knee to go into extension, i.e. movement that increases the angle across the knee between the upper leg and lower leg. This will naturally occur during gait, i.e., while the person using the brace is walking. Notably, the lock out mechanism of the free motion hinge gives the brace additional versatility in therapy. By contrast, when the lock out mechanism is not engaged, the patient has more natural walking freedom at the ankle. As a result, this invention assists the ankle to progress through different stages of therapy as the mobility of the ankle increases.

It should be noted that the present invention can be practiced otherwise than as specifically illustrated and described, without departing from its spirit or scope. It is intended that all such modifications and alterations be included insofar as they are consistent with the objectives and spirit of the invention.

What is claimed is:

1. An orthotic device for a joint of the human body at which a body part pivots, comprising:
    first, second and third members able to extend along respective posterior portions of the body part near the joint;
    a first connection joining the first member and the second member and providing an adjustable range of angular motion between the first member and the second member about a first axis; and
    a second connection joining the second member and the third member, providing a range of angular motion about a second axis substantially parallel to the first axis between the second member and the third member, and limiting plantar flexion about the second axis;
    wherein the second connection comprises:
        a hinge secured to the second member and the third member and centered at the second axis;
        a first bracket secured to the third member and including a first stop surface located eccentric of the second axis; and
        a second bracket secured to the second member and including a second stop surface located eccentric of the second axis and being able to contact the first stop surface; and
    wherein the first connection comprises:
        a first surface formed on the first member and having an arcuate shape centered at the first axis;
        a second surface formed on the second member, overlapping the first surface, and having an arcuate shape centered at the first axis; and
        an attachment for permitting the first surface and the second surface to rotate about the first axis, and for mutually securing the first surface and the second surface.

2. An orthotic device for a joint of the human body at which a body part pivots, comprising:
    first, second and third members able to extend along respective posterior portions of the body part near the joint;
    a first connection joining the first member and the second member and providing an adjustable range of angular motion between the first member and the second member about a first axis; and
    a second connection joining the second member and the third member, providing a range of angular motion about a second axis substantially parallel to the first axis between the second member and the third member, and limiting plantar flexion about the second axis; and
    wherein the second connection comprises:
        a hinge secured to the second member and the third member and centered at the second axis;
        a first bracket secured to the third member and including a first stop surface located eccentric of the second axis; and
        a second bracket secured to the second member and including a second stop surface located eccentric of the second axis and being able to contact the first stop surface; and
    wherein the first connection comprises:
        a first surface located on the first member and formed in a first arc with a first slotted hole centered at the first axis and extending along the first arc;
        an second surface located on the second member, overlapping the first arc, formed in a second arc with a second slotted hole, aligned with the first slotted hole, centered at the first axis and extending along the second arc; and
        an attachment that extends through the first and the second slotted holes for permitting the first surface and the second surface to rotate about the first axis, and for mutually securing the first surface and the second surface.

3. An orthotic device for a joint of the human body at which a body part pivots, comprising:
    first, second and third members able to extend along respective posterior portions of the body part near the joint;
    a first connection joining the first member and the second member and providing an adjustable range of angular motion between the first member and the second member about a first axis; and
    a second connection joining the second member and the third member, providing a range of angular motion about a second axis substantially parallel to the first axis between the second member and the third member, and limiting plantar flexion about the second axis; and
    wherein the second connection comprises:

a hinge secured to the second member and the third member and centered at the second axis;
a first bracket secured to the third member and including a first stop surface located eccentric of the second axis;
a second bracket secured to the second member and including a second stop surface located eccentric of the second axis and being able to contact the first stop surface; and
wherein the first connection comprises:
a first surface formed on the first member and having an arcuate shape centered at the first axis;
an outer block overlapping the first surface;
a second surface formed on the second member, overlapping and contacting the first member, and having an arcuate shape centered at the first axis;
an inner block overlapping the second member; and
an attachment engaged with the outer block and including a threaded shank extending through the first member and the second member, and a nut contacting the inner block and engaged with the threaded shank, the attachment being released to permit the first surface and the second surface to rotate about the first axis, and being engaged to secure mutually the first surface and the second surface.

4. An orthotic device for a joint of the human body at which a body part pivots, comprising:
first, second and third members able to extend along respective posterior portions of the body part near the joint;
a first connection joining the first member and the second member and providing an adjustable range of angular motion between the first member and the second member about a first axis; and
a second connection joining the second member and the third member, providing a range of angular motion about a second axis substantially parallel to the first axis between the second member and the third member, and limiting plantar flexion about the second axis; and
wherein the second connection comprises:
a hinge secured to the second member and the third member and centered at the second axis;
a first bracket secured to the third member;
a second bracket secured to the second member; and
a screw engaged with the second bracket and the first bracket for mutually securing the first bracket and the second bracket against pivoting about the second axis.

5. An orthotic device for a joint of the human body at which a body part pivots, comprising:
first, second and third members able to extend along respective posterior portions of the body part near the joint;
a first connection joining the first member and the second member and providing an adjustable range of angular motion between the first member and the second member about a first axis; and
a second connection joining the second member and the third member, providing a range of angular motion about a second axis substantially parallel to the first axis between the second member and the third member, and limiting plantar flexion about the second axis; and
wherein the second connection further comprises:
a hinge secured to the second member and the third member and centered at the second axis;
a first bracket secured to the third member and including a stop surface located eccentric of the second axis;
a second bracket secured to the second member;
a screw; and
a spring secured to the second bracket, aligned with the screw and extending toward the stop surface, contact between the spring and the stop surface providing elastic resistance to movement of the third member about the second axis, the screw being engageable with the second bracket and the first bracket for mutually securing the first bracket and the second bracket against pivoting about the second axis.

6. An orthotic device for a leg of the human body, comprising:
a support having a length adapted to extend along a posterior portion of a length of a calf of the leg and including a pocket;
a first member adapted to extend along the posterior portion of the length of the calf and able to fit within the pocket and to be secured to the support;
a second member and a third member adapted to extend along respective posterior portions of an ankle and heel of the leg;
a first connection joining the first member and the second member, and providing an adjustable range of angular motion about a first axis between the first member and the second member; and
a second connection spaced from and located at a lower elevation than an elevation of the first connection, joining the second member and the third member, providing a range of angular motion about a second axis substantially parallel to the first axis between the second member and the third member, and including a first surface secured to the second member and a second surface secured to the third member, mutual bearing contact of the first and second surfaces limiting plantar flexion about the second axis.

7. The orthotic device of claim 6, wherein the second connection comprises:
a hinge secured to the second member and the third member and centered at the second axis;
a first bracket secured to the third member and including a first stop surface located eccentric of the second axis;
a second bracket secured to the second member and including a second stop surface located eccentric of the second axis and being able to contact the first stop surface.

8. The orthotic device of claim 7, wherein the first connection comprises:
a first surface formed on the first member and having an arcuate shape centered at the first axis;
a second surface formed on the second member, overlapping the first surface, and having an arcuate shape centered at the first axis; and
an attachment for permitting the first surface and the second surface to rotate about the first axis, and for mutually securing the first surface and the second surface.

9. The orthotic device of claim 7, wherein the first connection comprises:
a first surface located on the first member, formed in a first arc with a first slotted hole centered at the first axis and extending along the first arc;
an second surface located on the second member, overlapping the first arc, formed in a second arc with a second slotted hole, aligned with the first slotted hole, centered at the first axis and extending along the second arc; and
an attachment that extends through the first and second slotted holes for permitting the first surface and the second surface to rotate about the first axis, and for mutually securing the first surface and the second surface.

10. The orthotic device of claim 7, wherein the first connection comprises:
a first surface formed on the first member and having an arcuate shape centered at the first axis;
an outer block overlapping the first member;
a second surface formed on the second member, overlapping and contacting the first surface, and having an arcuate shape centered at the first axis;
an inner block overlapping the second member; and
an attachment that engages the outer block and includes a threaded shank extending through the first member and the second member, and a nut contacting the inner block and engaged with the threaded shank, the attachment being released to permit the first surface and the second surface to rotate about the first axis, and being engaged to secure mutually the first surface and the second surface.

11. The orthotic device of claim 6, wherein the second connection comprises:
a hinge secured to the second member and the third member and centered at the second axis;
the third member further including a first stop surface located eccentric of the second axis; and
the second member including a second stop surface located eccentric of the second axis and being able to contact the first stop surface.

12. The orthotic device of claim 6, wherein the second connection comprises:
a hinge secured to the second and third members, and said hinge being centered at the second axis;
a first bracket secured to the third member and including a first stop surface located eccentric of the second axis;
a second bracket secured to the second member and including screw threads and a second stop surface located eccentric of the second axis; and
a screw engaged with the screw threads for securing the first and second stop surfaces in mutual contact when the second connection is in an extended position.

13. The orthotic device of claim 6, wherein the second connection comprises:
a hinge secured to the second member and the third member and centered at the second axis;
a first bracket secured to the third member;
a second bracket secured to the second member; and
a screw engaged with the second bracket and the first bracket for mutually securing the first bracket and the second bracket against pivoting about the second axis.

14. The orthotic device of claim 6, wherein the second connection comprises:
a hinge secured to the second and third members, and being centered at the second axis;
a first bracket secured to the third member and including a stop surface located eccentric of the second axis;
a second bracket secured to the second member;
a screw; and
a spring secured to the second bracket, aligned with the screw and extending toward the stop surface, contact between the spring and the stop surface providing elastic resistance to movement of the third member about the second axis, the screw being engageable with the second bracket and the first bracket for mutually securing the first bracket and the second bracket against pivoting about the second axis.

15. An orthotic device for a joint of the human body at which a body part pivots, comprising:
first, second and third members, each member adapted to be located at a posterior portion of the body part;
a first connection joining the first member and the second member and defining a first axis about which the first member and the second member pivot through an adjustable range of angular motion; and
a second connection joining the second member and the third member, and defining a second axis substantially parallel to the first axis, about which second axis the second member and the third member pivot through a second range of angular motion freely in a first direction, and against elastic resistance before coming into contact with a stop surface that limits plantar flexion in a second direction which is opposite the first direction; and
a support including an inner surface having a length adapted to extend along a portion of a leg calf, and a pocket located at an outer surface of the support and sized to receive an upper portion of the first member therein.

16. An orthotic device for a joint of the human body at which a body part pivots, comprising:
first, second and third members able to extend along respective posterior portions of the body part near the joint;
a first connection joining the first member and the second member and providing an adjustable range of angular motion between the first member and the second member about a first axis;
a second connection joining the second member and the third member, providing a range of angular motion about a second axis between the second member and the third member, limiting plantar flexion about the second axis and further comprising:
a hinge secured to the second member and the third member and centered at the second axis;
a first bracket secured to the third member and including a stop surface located eccentric of the second axis;
a second bracket secured to the second member;
a screw; and
a spring secured to the second bracket, aligned with the screw and extending toward the stop surface, contact between the spring and the stop surface providing elastic resistance to movement of the third member about the second axis, the screw being engageable with the second bracket and the first bracket for mutually securing the first bracket and the second bracket against pivoting about the second axis.

17. An orthotic device for a leg of the human body, comprising:
a support having a length adapted to extend along a posterior portion of a length of a calf of the leg and including a pocket;
a first member adapted to extend along the posterior portion of the length of the calf and able to fit within the pocket and to be secured to the support;
a second member and a third member adapted to extend along respective posterior portions of an ankle and heel of the leg;
a first connection joining the first member and the second member, and providing an adjustable range of angular motion about a first axis between the first member and the second member; and
a second connection spaced from and located at a lower elevation than an elevation of the first connection, joining the second member and the third member, providing a range of angular motion about a second axis between the second member and the third member, and including first and second surfaces located such that mutual bearing contact of the first and second surfaces limiting plantar flexion about the second axis, the second connection further comprising:
a hinge secured to the second and third members, and being centered at the second axis;
a first bracket secured to the third member and including a stop surface located eccentric of the second axis;
a second bracket secured to the second member;
a screw; and
a spring secured to the second bracket, aligned with the screw and extending toward the stop surface, contact between the spring and the stop surface providing elastic resistance to movement of the third member about the second axis, the screw being engageable with the second bracket and the first bracket for mutually securing the first bracket and the second bracket against pivoting about the second axis.

* * * * *